United States Patent
Wang et al.

(10) Patent No.: US 9,956,340 B2
(45) Date of Patent: May 1, 2018

(54) VENTED IMPLANTABLE DRUG-DELIVERY DEVICE AND RELATED METHODS

(71) Applicants: Bin Wang, Arcadia, CA (US); Jason Shih, Yorba Linda, CA (US); Gregory Harbers, Valencia, CA (US); Fukang Jiang, Arcadia, CA (US); Sean Caffey, Pasadena, CA (US)

(72) Inventors: Bin Wang, Arcadia, CA (US); Jason Shih, Yorba Linda, CA (US); Gregory Harbers, Valencia, CA (US); Fukang Jiang, Arcadia, CA (US); Sean Caffey, Pasadena, CA (US)

(73) Assignee: MINIPUMPS, LLC, Pasadena, CA (US)

( * ) Notice: Subject to any disclaimer, the term of this patent is extended or adjusted under 35 U.S.C. 154(b) by 0 days. days.

(21) Appl. No.: 14/307,063

(22) Filed: Jun. 17, 2014

(65) Prior Publication Data
US 2014/0371674 A1    Dec. 18, 2014

Related U.S. Application Data

(60) Provisional application No. 61/835,832, filed on Jun. 17, 2013.

(51) Int. Cl.
*A61M 5/155* (2006.01)
*A61M 31/00* (2006.01)
(Continued)

(52) U.S. Cl.
CPC ........... *A61M 5/155* (2013.01); *A61L 31/048* (2013.01); *A61L 31/14* (2013.01);
(Continued)

(58) Field of Classification Search
CPC ............. A61M 5/155; A61M 5/14276; A61M 5/14212; A61M 5/14; A61M 5/38;
(Continued)

(56) References Cited

U.S. PATENT DOCUMENTS

| | | | | |
|---|---|---|---|---|
| 4,511,355 A | * | 4/1985 | Franetzki | A61M 5/14276 128/DIG. 12 |
| 4,734,092 A | * | 3/1988 | Millerd | A61M 5/14248 128/DIG. 12 |

(Continued)

OTHER PUBLICATIONS

Wikol, Michael, Bryce Hartman, Joseph Brendle, Michele Crane, Uwe Beuscher, Jeff Brake, and Tracy Shickel. "Expanded Polytetrafluoroethylene Membranes and Their Applications." W. L. Gore & Associates, Inc., Dec. 5, 2008. Web. Sep. 24, 2015. <https://web.archive.org/web/20081205044512/http://www.gore.com/MungoBlobs/827/932/ExpandedPTFEandTheirMembran.*

(Continued)

*Primary Examiner* — Bhisma Mehta
*Assistant Examiner* — James D Ponton
(74) *Attorney, Agent, or Firm* — Morgan, Lewis & Bockius LLP

(57) ABSTRACT

An implantable device has an outer shell that includes an aperture through the housing of the device and, spanning the aperture, a membrane structure permeable to gas but not to liquid. In this way, excess gas may be vented from the device. The membrane and aperture are designed to discourage or even prevent tissue ingrowth.

15 Claims, 4 Drawing Sheets

(51) Int. Cl.
*A61L 31/14* (2006.01)
*A61L 31/04* (2006.01)
*A61M 5/142* (2006.01)
*A61M 5/145* (2006.01)

(52) U.S. Cl.
CPC .... *A61M 5/14212* (2013.01); *A61M 5/14276* (2013.01); *A61M 31/002* (2013.01); *A61M 5/14593* (2013.01); *A61M 2005/14204* (2013.01)

(58) Field of Classification Search
CPC ................ A61M 31/002; A61M 5/145; A61M 2005/1401; A61M 5/14593
See application file for complete search history.

(56) References Cited

U.S. PATENT DOCUMENTS

| | | | | |
|---|---|---|---|---|
| 5,090,963 A * | 2/1992 | Gross | ................... | A61M 5/155 128/DIG. 12 |
| 5,186,805 A * | 2/1993 | Gross | ................... | A61M 5/155 204/265 |
| 5,242,406 A * | 9/1993 | Gross | ................... | A61M 5/155 128/DIG. 12 |
| 6,520,936 B1 * | 2/2003 | Mann | ................ | A61M 5/14276 604/141 |
| 6,521,012 B2 * | 2/2003 | Lamon | ................ | B01D 53/228 427/255.6 |
| 2006/0255063 A1 * | 11/2006 | Gallnbock | .......... | A61M 5/1483 222/95 |
| 2010/0022992 A1 * | 1/2010 | Genosar | ............ | A61M 5/14248 604/891.1 |
| 2011/0202032 A1 * | 8/2011 | Shih | ...................... | A61F 9/0017 604/500 |

OTHER PUBLICATIONS

"EPTFE Membranes." (n.d.): n. pag. GE Healthcare Life Sciences, Feb. 2013. Web. Sep. 24, 2015. <https://web.archive.org/web/20150925134315/https://www.gelifesciences.com/gehcls_images/GELS/Related%20Content/Files/1362565656329/litdoc29039989_20130319211559.pdf>.*

* cited by examiner

VENTED IMPLANTABLE DRUG-DELIVERY DEVICE AND RELATED METHODS

CROSS-REFERENCE TO RELATED APPLICATIONS

The present application claims priority to, and the benefits of, U.S. Ser. No. 61/835,832, filed on Jun. 17, 2013, the entire disclosure of which is hereby incorporated by reference.

FIELD OF THE INVENTION

In various embodiments, the present invention relates generally to implantable medical devices and, more specifically, to devices in which a pressure offset is created within the device or at the interface between the device and its surroundings.

BACKGROUND

Implantable drug-delivery devices typically utilize an actuation mechanism to drive medicament from a reservoir through a cannula into target areas. The actuation mechanism may be pressure-driven or cause pressure changes within the drug-delivery device or at the interface between the device and its surroundings. The pressure magnitudes and gradients in these regions can make it difficult to precisely control delivery of small amounts of drug, especially when the device is refillable or used for repeated dosing over a relatively long period. For example, without proper regulation of the pressure in the drug reservoir, pressure or vacuum buildup can interfere with smooth, continuous administration of a liquid medicament. This problem is particularly acute in devices whose driving mechanism involves generation of pressurized gas. In such devices, excess gas can leak to various device regions. More generally, when the device is implanted in a patient, the difficulties of limited physical space and access to the device, as well as the overall complexity of in vivo implantation and operation, can make pressure regulation in the device essential and exacerbate the problems arising from inadequate regulation.

Gas-driven drug-delivery devices may produce excess gas, and ensuring gas-tightness along the pressurization route can require significant efforts in design, manufacture and quality control. For example, in electrolytic drug-delivery devices, hydrogen and oxygen are generated as an actuating mechanism during dosing. Hydrogen is known to penetrate thin walls easily and leak into reservoir chambers and their perimeters, resulting in inaccurate pressure-dosing characteristics or even unintended delivery of gas. For some drug-delivery regimes, instantaneous bursts of drug may be required (alone or to supplement steady-state delivery). The excess gas and its effects on delivery accuracy can be pose major challenges, especially in the sub-milliliter scale.

Excess gas can also adversely affect the refilling of drug-delivery devices. As excess gas accumulates in the drug reservoir chambers, refill routes, and/or other adjacent interior spaces, it can complicate the refilling process and create considerable dead volume. More importantly, some drug-delivery devices have compliant reservoir walls to minimize dead volumes and provide ease in handling during refilling. With these devices, the excess gas accumulating in the perimeter creates a differential pressure that can eventually prevent the refilling operation from proceeding to completion.

Venting may seem like an obvious solution to unwanted gas buildup, but can be difficult to achieve in devices intended for implantation. While valved passages connecting the pump to a region outside of the device body have been proposed for managing excess gas in drug-delivery devices, such an approach is often unsuitable for biomedical implants, as the transport of gases through the human body via a catheter or artificial vehicle for venting may be painful and increase risk of infection. In addition, as most biomedical implants are highly integrated and miniaturized, the limited physical space and access to the device further complicates venting: the venting component in an implantable drug-delivery device must generally be compact, easy to integrate and, notably, compatible with the anatomic environment in which various body fluids and tissues may interact with the vent.

One possible approach to venting an implantable drug-delivery device is to connect additional gas-filled space to the region of excess gas accumulation in order to buffer abrupt pressure changes inside the device. This may be additional space within the device itself or a chamber that is tethered by a fluidic connection but external to the main drug-delivery device. This approach, however, requires a relatively large space that may be impractical for biomedical applications that demand space efficiency. Additionally, without a passage through which excess gas may be expelled from the device, pressure will continue to build up within, and potentially overwhelm, the buffer volume. Another possible approach would employ a gas-permeable outer shell to expel excess gas. This approach, however, would pose challenges of material choice, fabrication complexity, fabrication cost, and compromised mechanical strength of the surface. Furthermore, pores that confer gas permeability can also allow for tissue ingrowth that may block a sufficient number of the pores to compromise their effectiveness.

SUMMARY

Embodiments of the invention utilize a selectively permeable membrane structure integrated in the outer shell and/or in other areas of an implantable drug-delivery device. In various embodiments, the device includes an aperture through the housing of the device and, spanning the aperture, a membrane structure permeable to gas but not to liquid. In this way, excess gas may be vented from the device. The membrane and aperture are designed to discourage or even prevent tissue ingrowth.

Accordingly, in a first aspect, the invention pertains to an implantable device for administering a liquid. In various embodiments, the device comprises a housing including an aperture therethrough; within the housing, a pump assembly including a reservoir, a gas-driven forcing mechanism and a cannula for conducting liquid from the reservoir to an ejection site exterior to the housing in response to pressure applied by the forcing mechanism; and external to the pumping mechanism but within the housing and spanning the aperture, a membrane structure comprising a gas-permeable membrane and at least one support layer attached thereto. The membrane structure is permeable to gas but not to liquid at least within the area thereof exposed by the aperture.

In various embodiments, the membrane structure, at least within the area thereof exposed by the aperture, has a pore size sufficiently small to prevent tissue ingrowth and endotheliazation. Furthermore, the membrane structure may have a pore size that allows gas to flow therethrough at a sufficient rate to substantially offset a positive pressure or vacuum pressure applied to the device. The membrane structure may be biocompatible. At least the surface of the membrane structure exposed by the aperture may comprise an oleophobic coating thereover. For example, the membrane structure may comprise or consist essentially of ePTFE.

At least a portion of the membrane structure surface may comprise (e.g., have coated thereon) an adhesive material for affixation to an interior surface of the housing. A portion of the membrane structure may be bonded to an interior surface of the housing with an epoxy. The membrane structure may have a thickness less than 500 µm.

In some embodiments the support layer(s) is/are perforated. For example, the support layer(s) may be perforated with clusters of holes each having a diameter in the range of 50-400 µm. The support layer(s) may be substantially rigid. In various embodiments, the support layer(s) comprise or consist essentially of one or more of polypropylene, polyethylene, polyvinylidene fluoride, poly(methyl methacrylate), or polyether ether ketone. In some embodiments, the support layer(s) comprise or consist essentially of one or more of spunbond fabric, a woven fabric, an extruded film, a cast film, a blown film or an injection-molded film.

Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, structures, routines, steps, or characteristics may be combined in any suitable manner in one or more examples of the technology. The headings provided herein are for convenience only and are not intended to limit or interpret the scope or meaning of the claimed technology. The term "substantially" or "approximately" means ±10% (e.g., by weight or by volume), and in some embodiments, ±5%.

BRIEF DESCRIPTION OF THE DRAWINGS

In the drawings, like reference characters generally refer to the same parts throughout the different views. Also, the drawings are not necessarily to scale, with an emphasis instead generally being placed upon illustrating the principles of the invention. In the following description, various embodiments of the present invention are described with reference to the following drawings, in which.

DETAILED DESCRIPTION

Embodiments of the present invention provide a vent solution based on a selectively permeable membrane structure integrated into the rigid outer shell of an implantable drug-delivery device. Although the ensuing discussion focuses on the integration into the outer shell, this vent solution may be deployed in other areas of the implantable drug-delivery device that may require venting (e.g., the refill port). Additionally, it should be understood that the selectively permeable membrane structure may be placed above or below any surface of a drug-delivery device that is perforated or allows for some form of fluid/gas permeation.

Figure 1A:
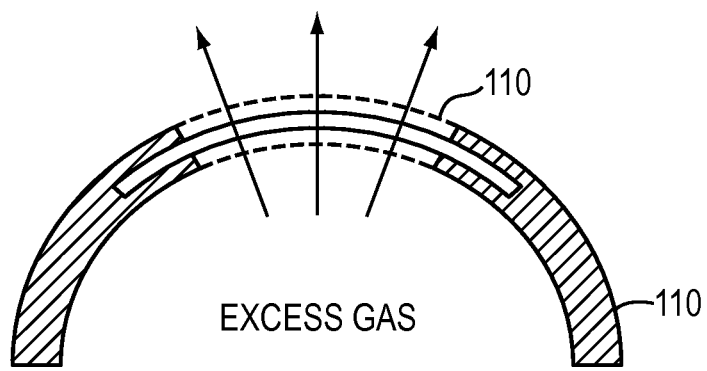
FIG. 1A schematically illustrates the outer shell of a device in accordance with the present invention, the outer shell including a selectively permeable membrane structure.
Figure 1B:
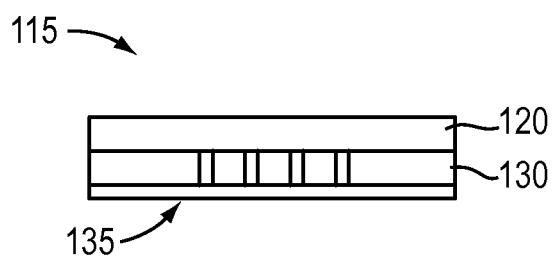
FIG. 1B is an elevation of an embodiment of the selectively permeable membrane structure.

With reference to FIGS. 1A and 1B, the outer shell 100 of an implantable device that generates excess gas is provided with a vent 110, which comprises or consists of an aperture through the shell 100 and, coextensive with or (more typically) extending beyond the perimeter of the aperture, a selectively permeable membrane structure. The rigid shell 100 may be made of a metal such as titanium or may consist of, or include, a biocompatible plastic material alternatively or in addition. More generally, the shell 100 may include or consist essentially of one or more of a ceramic, an epoxy encapsulation, a metal (e.g., titanium (Ti), niobium (Nb), or tantalum (Ta)), polyetherether ketone (PEEK), polypropylene, polydimethylsiloxane (PDMS), or parylene. For example, the shell may be at least partially coated with parylene.

The membrane structure 115, a representative embodiment of which is illustrated in FIG. 1B, may have multiple layers comprising or consisting of a functional layer (i.e., a gas-permeable membrane) 120 and one or more support layers 130. For example, the permeable layer 120 may be a membrane laminated onto a plastic thin film as a backing layer 130. The support layer 130 may have a series of perforations 135 to permit the passage of gas through the functional layer 120. Alternatively, the support layer 130 may have a single large opening or multiple large slots beneath a portion of the functional layer 120 through which gas is released.

Additional layers can also be incorporated for improved adhesion to the device outer shell 100 and enhanced overall mechanical strength of the vent port 110. Other suitable adhesion techniques known in the field of implantable medical devices may also be used. For example, a biocompatible epoxy may be used to join the gas-permeable layer 120 to the backing layer(s) 130, as well as to join the resulting structure 115 to the outer shell 100 of the implantable pump device as shown in greater detail below. The layer(s) of the structure 120 that actually adheres to the shell 100 can undergo surface treatment such as sandblasting and/or plasma bombardment to improve adhesion when using biocompatible epoxy.

Figure 2:
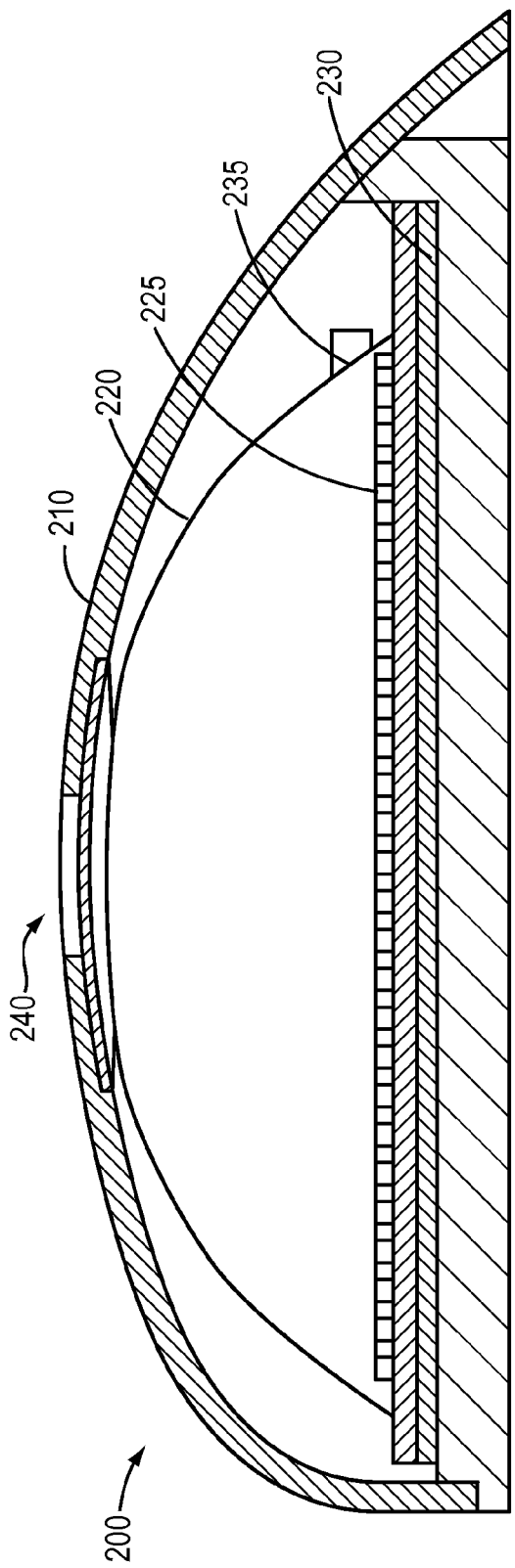
FIG. 2 is a sectional elevation of a representative drug-delivery device including an embodiment of the invention.
Figure 3:
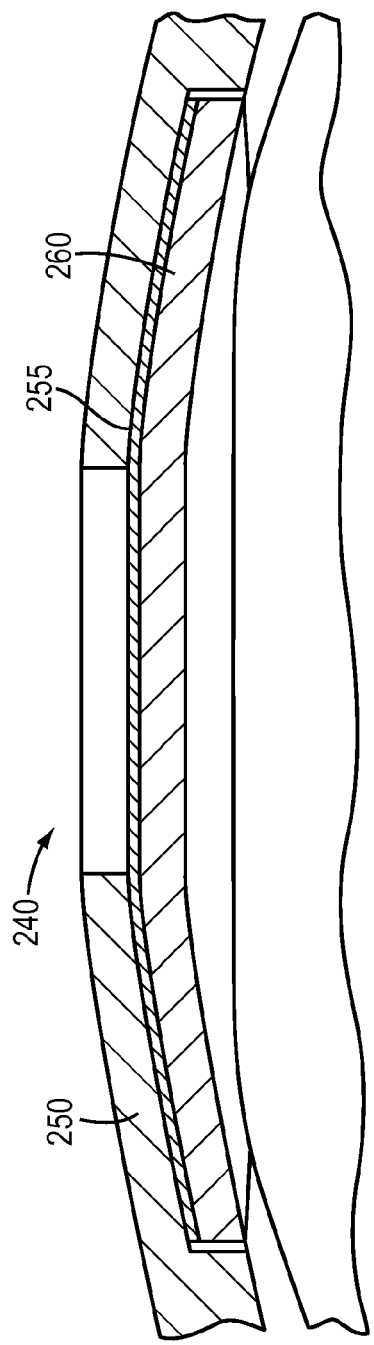
FIG. 3 is an enlarged portion of the elevation shown in FIG. 2.
Figure 4:
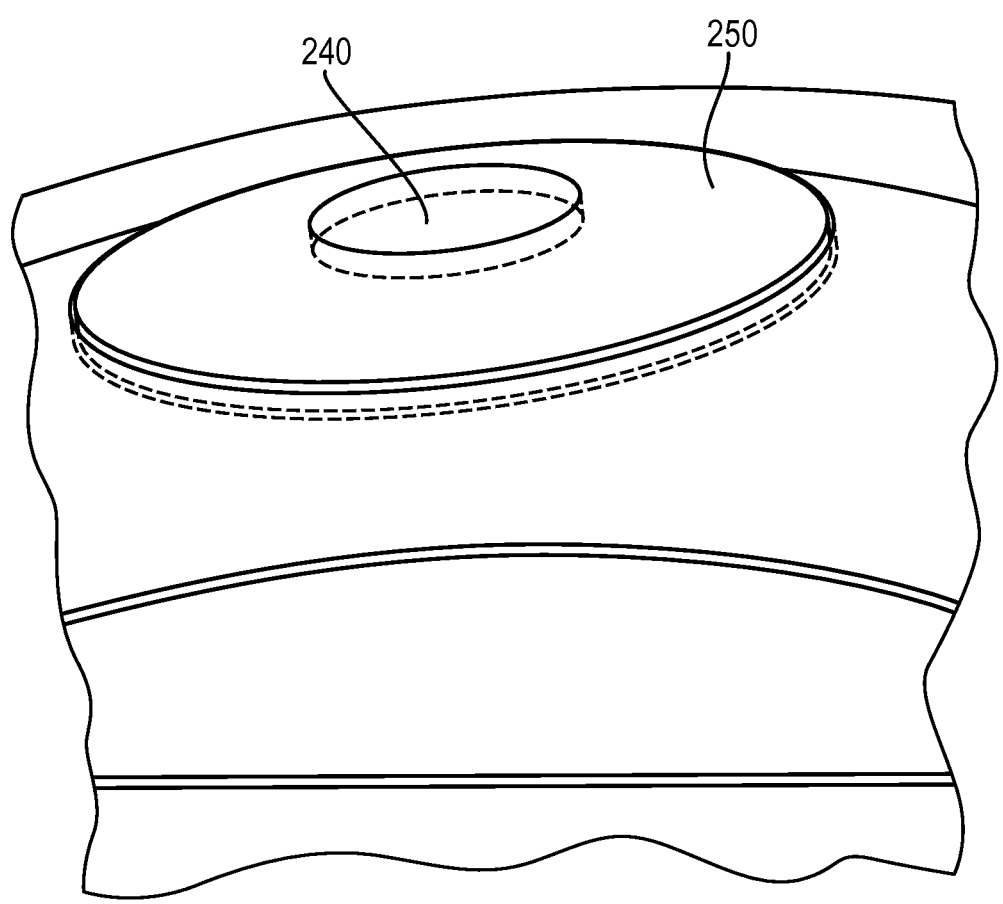
FIG. 4 is an enlarged perspective view of an aperture spanned by the selectively permeable membrane structure.

FIGS. 2-5 show a representative deployment of the invention in an implantable electrolytic drug pump 200. With reference to FIGS. 2-4, the pump 200 includes a hard outer shell 210, which may be made of, for example, titanium. Within the shell 210 is a dome-shaped structure 220, which may be formed from a hard polymer, such as acrylic or metals such as titanium, aluminum or other biocompatible material. Alternatively, the dome-shaped structure 220 may be made of a shape-retaining but compliant material such as parylene; at a thickness of 100 µm, for example, it is found that a parylene structure 220 maintains its shape but is capable of slight flexure under pressure. A combination of the foregoing materials may also be used by coating with parylene any surfaces that may contact drug or bodily fluids. At the floor of the dome 220 is a corrugated, expandable membrane 225, which may be made of parylene, silicone or other suitably flexible material. Beneath the membrane 225 is a set of electrolysis electrodes on a floor 230, and an electrolysis liquid is contained within the space formed by the floor 230 and the expandable membrane 225. The space between the expandable membrane 225 and the dome 220 contains the drug to be dispensed; a cannula 235 is in fluid communication with this interior space (i.e., drug chamber). As best seen in FIGS. 3 and 4, an aperture 240 extends through the shell 210, and beneath the aperture 240 is a selectively permeable membrane structure 250 including a gas-permeable, liquid-impermeable functional layer 255 and a support layer 260. As noted earlier, the support layer 260 may have perforations or an enlarged opening within the aperture 240 to permit gas to flow through the functional layer and out the aperture. As shown in FIG. 4, the upper surface of the membrane structure 250 is bonded to the interior surface of the dome 220. In some embodiments, the peripheral edge of the support layer 260 extends beyond that of the functional layer 255, and it is the exposed annular upper surface of the support layer 260 that is actually adhered to the dome 220.

Various other embodiments may incorporate the one or more of the functional and support layers into the shell by various methods. In one embodiment, the aperture is tiered into one or more steps, and each layer or subset of layers may be incorporated to be flush with the subsequent step in the aperture. Alternative approaches to adhering and securing the layers such as the use of pins, screws, or tabs may be employed to bond the layers and integrate the membrane structure into the dome.

Figure 5:
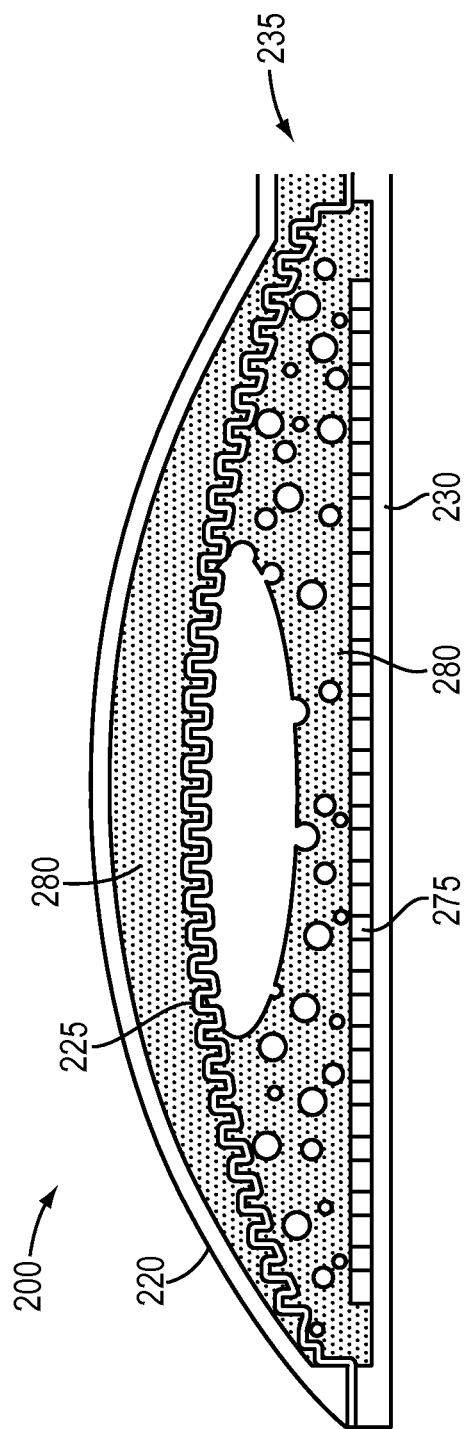
FIG. 5 is a sectional elevation of a representative drug-delivery device illustrating its mode of operation.

The operation of the pump device 200 is illustrated in FIG. 5. Upon activation of the electrodes 275, gas is evolved from the liquid in the electrolysis chamber 280 (which is bounded by the floor 230 and the expandable membrane 225), inflating the membrane 225 and thereby reducing the volume of the drug chamber 280, forcing liquid therein out through the cannula 235. The cannula 235 may be equipped with a check valve and/or a flow sensor. Suitable control circuitry and a battery (not shown) may be mounted on a circuit board integrated into the bottom portion of the housing 210; see, e.g., U.S. Pat. Nos. 8,285,328 and 8,231,608, the entire disclosures of which are hereby incorporated by reference. In some embodiments, the electrodes 275 are etched, printed, or otherwise deposited directly onto the circuit board for cost-savings and ease of manufacturing.

Gas penetrating the dome structure 220 and accumulating in the dead space between that structure and the hard shell 210 is vented through the aperture 240, which, again, is spanned by the gas-permeable membrane structure 250 as described above.

The functional layer 120 of the membrane structure 115 desirably has a high permeability to most gases to allow for rapid gas transit but is virtually impermeable to liquid, preventing the intrusion of, for example, aqueous fluids. The pore diameter of the layer 120 is chosen to be much smaller (e.g., orders of magnitude smaller) than the typical pore size that would permit tissue ingrowth and endothelialization, so that the ingrowth of soft tissues in the vent can be minimized. Although the minimum pore size permitting tissue ingrowth depends on the surrounding tissue, in general it ranges from ~10 µm to a few mm (which is much greater than the permeable membrane pore size required to create adequate gas permeability).

Typically, the support layer 130 is one or more layers of solid thin film with adequate mechanical strength and a surface bondable to the interior wall of the shell 210. Depending on the material used, the support layer 130 can be as-manufactured (e.g., if porous) or intentionally perforated, as discussed above, at least in the venting area for unobstructed gas passage. As a result, even a small aperture 240 is capable of releasing excess gas at a reasonably high rate under a low differential pressure. In addition, the surface of membrane structure 115 within the aperture 240 may be treated to impart or enhance oleophobicity in order to reject molecules in human body fluids (e.g., proteins, lipids, and blood cells) that might interfere with gas exchange. One example surface coating is super-hydrophobic reagent such as a monolayer of TEFLON. With these attributes, the venting arrangement of the present invention provides rapid pressure equilibration between the internal space of the device and the human body environment where the device is implanted for long-term applications. Its function does not require direct access to the device 200 for manipulation of the gas-driving components.

The materials of the permeable membrane 120 and the backing layer(s) 130 are chosen based on both the functionalities and the biomedical compatibility. The gas-permeable membrane 120 can be expanded polytetrafluoroethylene (ePTFE) with a pore diameter on the scale of submicrons. Alternatively, TEFLON AF or other materials having (or which can be manipulated to have) an inter-nodal distance that is permeable to gas but not liquid may be employed.

The gas-permeable membrane 120 may further be altered to enhance robustness while maintaining acceptable gas flow rates. One approach is to use a thicker membrane or to create a thicker membrane by stacking multiple layers of membranes. In one embodiment an ePTFE membrane with a pore diameter between 0.2-0.6 µm and an intermodal distance of 10 µm and a thickness of over 600 µm exhibited a mass flow rate of over 0.5 mL/min under a driving pressure below 0.05 psi.

This driving pressure has been calculated to be more than sufficient to drive the gas flow through the gas-permeable membrane 120. By using ideal gas law, PV=nRT, the equation of $PV_1 = P'(V1 + \Delta V)$ shows the pressure change caused by a change in pressure that occurs as incremental amounts of drug are pumped from the reservoir. Thus, $\Delta P = \Delta V/(V_1 + \Delta V)P$, where P=atmospheric pressure (14.7 psi), $\Delta V$=change in mass of the drug reservoir, and $V_1$=space between the dome 220 and the hard shell 110. In one embodiment, the drug reservoir is filled to 300 µL, leaving $V_1$=200 µL. A dose of 50 µL creates a pressure change of 50/(200+50)14.7 psi=2.94 psi. Applying this pressure differential to the above embodiment of an ePTFE membrane, an adequate gas flow rate is achieved.

In embodiments where a vacuum is created in the space between the dome 220 and the hard shell 110 with each subsequent dose, the vacuum may be offset by drawing gas in through the gas-permeable membrane. In certain implant positions, the vacuum may not be offset if adequate gas cannot be drawn in from the environment. However, the vacuum is beneficial in that it promotes refilling, which is inhibited by gas accumulation in the space between the dome and the hard shell. This gas is vented out through the gas-permeable membrane.

The backing layer(s) 130 can be any one or more of various plastic thin films including polypropylene, polyethylene, polyvinylidene fluoride (PVDF), poly(methyl methacrylate) (PMMA), and PEEK. The backing layer(s) can take the form of a spunbond or woven fabric with intrinsic gas permeability, or extruded, cast, blown, or injection-molded solid films perforated with clusters of holes (at least where the layer will face the hard-shell aperture) each having a diameter in the range of 50-400 µm. The overall thickness of the membrane structure 115 can be smaller than 500 µm.

The backing layer 130 may further be altered to enhance robustness while maintaining acceptable gas-flow rates. According to principles of material strength, the deflection of an edge-clamped plate is highly related to its diameter. By using a refined perforation pattern on the support, the membrane deformation under pressurization/vacuum can be minimized. The porosity typically reduces with hole diameter, which can be expressed by a model featuring an array of uniformly distributed holes:

$$\text{porosity} = \frac{\pi (d_{hole}/2)^2}{(d_{spacing} + d_{hole})^2}$$

While the hole diameter can be further minimized by using advanced techniques such as deep-UV laser drilling, the spacing of holes is primarily limited due to both technical and economical reasons. For example, a hole diameter of 5 µm and typical spacing of 20 µm results in a porosity of approximately 3%. Because of the gas permeability of the venting membrane, lower porosities within this range may be used while still enabling efficient venting.

In some embodiments, the membrane structure 115 is integrated into the same plane or applied to the internal or external surface of the implantable drug delivery device in different configurations. The membrane structure is not limited in terms of shape, size or orientation. For example, it may take the form of strips, circles, ovals, squares, or any other pattern. Furthermore, the layers of the membrane can be of different shapes and sizes to allow for better adhesion and provide a seamless integration with the surface of the implantable drug delivery device.

Certain embodiments of the present invention have been described above. It is, however, expressly noted that the present invention is not limited to those embodiments, but rather the intention is that additions and modifications to what was expressly described herein are also included within the scope of the invention. Moreover, it is to be understood that the features of the various embodiments described herein were not mutually exclusive and can exist in various combinations and permutations, even if such combinations or permutations were not made express herein, without departing from the spirit and scope of the invention. In fact, variations, modifications, and other implementations of what was described herein will occur to those of ordinary skill in the art without departing from the spirit and the scope of the invention. As such, the invention is not to be defined only by the preceding illustrative description.

The invention claimed is:

1. An implantable device for administering a liquid, the device comprising:
    a housing including an aperture therethrough;
    within the housing, a pump assembly including a reservoir, a gas-driven forcing mechanism and a cannula for conducting liquid from the reservoir to an ejection site exterior to the housing in response to pressure applied by the forcing mechanism, wherein at least a portion of gas generated by the gas-driven forcing mechanism penetrates the reservoir and accumulates in a space between the reservoir and the housing; and
    external to the pumping assembly but within the housing and spanning the aperture, a membrane structure comprising a gas-permeable membrane and at least one support layer attached thereto, the membrane structure being permeable to gas but not to liquid at least within an area thereof exposed by the aperture so as to allow the gas accumulated in the space between the reservoir and the housing to vent out through the gas-permeable membrane and the aperture;
    wherein the space between the reservoir and the housing is isolated from the liquid as it passes through the cannula.

2. The device of claim 1, wherein the membrane structure, at least within the area thereof exposed by the aperture, has a pore size sufficiently small to prevent tissue ingrowth and endotheliazation.

3. The device of claim 1, wherein the membrane structure has a pore size that allows gas to flow therethrough at a sufficient rate to substantially offset a positive pressure or vacuum pressure applied to the device.

4. The device of claim 1, wherein the membrane structure is biocompatible.

5. The device of claim 1, wherein at least the area of the membrane structure exposed by the aperture comprises an oleophobic coating thereover.

6. The device of claim 1, wherein the membrane structure comprises ePTFE.

7. The device of claim 1, wherein the at least one support layer is perforated.

8. The device of claim 7, wherein the at least one support layer is perforated with clusters of holes each having a diameter in the range of 50-400 µm.

9. The device of claim 1, wherein the at least one support layer is substantially rigid.

10. The device of claim 1, wherein the membrane structure has a surface, at least a portion of which comprises an adhesive material for affixation to an interior surface of the housing.

11. The device of claim 1, wherein a portion of the membrane structure is bonded to an interior surface of the housing with an epoxy.

12. The device of claim 1, wherein the at least one support layer comprises at least one of polypropylene, polyethylene, polyvinylidene fluoride, poly(methyl methacrylate), or polyether ether ketone.

13. The device of claim 1, wherein the at least one support layer comprises or consists essentially of a spunbond fabric, a woven fabric, an extruded film, a cast film, a blown film or an injection-molded film.

14. The device of claim 1, wherein the membrane structure has a thickness less than 500 µm.

15. The device of claim 1, further comprising a refill port, wherein the gas-permeable membrane is located at the refill port for venting the gas and thereby creating a vacuum pressure for promoting refilling.

* * * * *